US006180407B1

(12) United States Patent
Bernard et al.

(10) Patent No.: US 6,180,407 B1
(45) Date of Patent: *Jan. 30, 2001

(54) CLONING AND/OR SEQUENCING VECTOR (75) Inventors: Philippe Bernard; Philippe Gabant, both of Brussels (BE)

(73) Assignee: Universite Libre de Bruxelles, Brussels (BE)

( * ) Notice: Under 35 U.S.C. 154(b), the term of this patent shall be extended for 0 days.

This patent is subject to a terminal disclaimer.

(21) Appl. No.: 09/225,152

(22) Filed: Jan. 4, 1998

Related U.S. Application Data (63) Continuation-in-part of application No. 08/379,614, filed as application No. PCT/BE93/00051 on Aug. 2, 1993, now Pat. No. 5,910,438.

(30) Foreign Application Priority Data

Jul. 31, 1992 (BE) ................................................ 09200696

(51) Int. Cl.⁷ ............................ C12N 15/00; C12N 15/63
(52) U.S. Cl. ................ 435/471; 435/252.3; 435/252.33; 435/320.1; 435/480; 435/488
(58) Field of Search ............................ 435/252.3, 252.33, 435/320.1, 471, 480, 488

(56) References Cited

U.S. PATENT DOCUMENTS 5,910,438 * 6/1999 Bernard et al. .................... 435/252.3

FOREIGN PATENT DOCUMENTS

| PCT/BE93/ 00051 | 8/1993 | (WO) . |
| PCT/DK99/ 00258 | 5/1999 | (WO) . |

OTHER PUBLICATIONS

Philippe Bernard et al., The 41 carboxy–terminal residues of the miniF plasmid CcdA protein are sufficient to antagonize the killer activity of the CcdB protein, *Molecular & General Genetics*, vol. 226, No. 1/2, Apr. 1991, pp. 297–304.
Keystone Symposia on Molecular & Cellular Biology, *Journal of Cellular Biochemistry*, vol. 226, No. 3, Aug. 5, 1992, 2 pages.
James C. Pierce et al., A positive selection vector for cloning high molecular weight DNA by the bacteriophage P1 system: Improved cloning efficacy, Proceedings of the National Academy of Sciences of the United States of America, vol. 89, No. 6, Mar. 15, 1992, pp. 2056–2060.
Irene Kuhn et al., Positive–selection vectors utilizing lethality of the EcoRI endonuclease, *Gene*, vol. 44, 1986, pp. 253–263.
Bernhard Henrich et al., Use of the lysis gene of bacteriophage ØX174 for the construction of a positive selection vector, *Gene*, vol. 42, 1986, pp. 345–349.
Joseph Sambrook et al., Bacterial Hosts for Bacteriophage M13 Vectors, *Molecular Cloning*, Second Edition, 1989, 8 pages.

Philippe Bernard et al., Cell Killing by the F Plasmid CcdB Protein Involves Poisoning of DNA–Topoisomerase II Complexes, *Journal of Molecular Biology*, vol. 226, No. 3, 1992, pp. 735–745.
Philippe Bernard, Positive Selection of Recombinant DNA by CcdB, *Product Application Focus*, vol. 21, No. 2, Aug. 1996, pp. 320–323.
Panayiotis A. Ioannou et al., A new bacteriophage P1–derived vector for the propagation of large human DNA fragments, *Nature Genetics*, vol. 6, Jan. 1994, pp. 84–89.
Kenn Gerdes, Toxin–Antitoxin Modules May Regulate Synthesis of Macromolecules during Nutritional Stress, *Journal of Bacteriology*, vol. 182, No. 3, Feb. 2000, pp. 561–572.
Martine Couturier et al., Bacterial death by DNA gyrase poisoning, *Trends in Microbiology*, vol. 6, No. 7, Jul. 1998, pp. 269–275.
Marie Gotfredsen et al., The *Escherichia coli* relBE genes belong to a new toxin–antitoxin gene family, *Molecular Microbiology*, vol. 29, No. 4, 1998, pp. 1065–1076.
Suguru Tsuchimoto et al., Autoregulation by cooperative binding of the PemI and PemK proteins to the promoter region of the pem operon, *Molecular and General Genetics*, vol. 237, 1993, pp. 81–88.
María Jesús Ruiz–Echevarría et al., Structural and functional comparison between the stability systems ParD of plasmid R1 and Ccd of plasmid F, *Molecular and General Genetics*, vol. 225, 1991, pp. 355–362.
María Jesús Ruiz–Echevarría et al., The kis and kid genes of the parD maintenance system of plasmid R1 form an operon that is autoregulated at the level of transcription by the co–ordinated action of the Kis and Kid proteins, *Molecular Microbiology*, vol. 5, No. 11, 1991, pp. 2685–2693.
Michael B. Yarmolinsky, Programmed Cell Death in Bacterial Populations, *Science*, vol. 267, Feb. 10, 1995, pp. 836–837.
Anthony S. G. Smith et al., The poison–antidote stability system of the broad–host–range *Thiobacillus ferrooxidans* plasmid pTF–FC2, *Molecular Microbiology*, vol. 26, No. 5, 1997, pp. 961–970.
Roberts RC et al., The parDE operon of the broad–host–range plasmid RK2 specifies growth inhibition associated with plasmid loss, *Journal of Molecular Biology*, vol. 237, No. 1, Mar. 18, 1994, pp. 35–51.
Einat Aizenman et al., An *Escherichia coli* chromosomal "addiction module" regulated by 3',5'–bispyrophosphate: A model for programmed bacterial cell death, Proceedings of the National Academy of Sciences of the United States of America, vol. 93, Jun. 1996, pp. 6059–6063.
Hansjorg Lehnherr et al., Plasmid Addiction Genes of Bacteriophage P1: doc, which Causes Cell Death on Curing of Prophage, and phd, which Prevents Host Death when Prophage is Retained, *Journal of Molecular Biology*, vol. 233, 1993, pp. 414–428.

\* cited by examiner

*Primary Examiner*—Robert A. Schwartzman
(74) *Attorney, Agent, or Firm*—Knobbe, Martens, Olson & Bear, LLP (57) ABSTRACT

A cloning and/or sequencing vector enables recombinant clones to be selected directly. The vector encodes a fusion protein which includes a protein poison.

14 Claims, 1 Drawing Sheet

FIG. 1

SEQUENCE LISTING

<160> NUMBER OF SEQ ID NOS: 10

<210> SEQ ID NO 1
<211> LENGTH: 306
<212> TYPE: DNA
<213> ORGANISM: Artificial Sequence
<220> FEATURE:
<221> NAME/KEY: CDS
<222> LOCATION: (1)...(303)
<223> OTHER INFORMATION: ccdB gene of plasmid F.

<400> SEQUENCE: 1

```
atg cag ttt aag gtt tac acc tat aaa aga gag agc cgt tat cgt ctg      48
Met Gln Phe Lys Val Tyr Thr Tyr Lys Arg Glu Ser Arg Tyr Arg Leu
 1               5                  10                  15 ttt gtg gat gta cag agt gat att att gac acg ccc ggg cga cgg atg      96
Phe Val Asp Val Gln Ser Asp Ile Ile Asp Thr Pro Gly Arg Arg Met
             20                  25                  30 gtg atc ccc ctg gcc agt gca cgt ctg ctg tca gat aaa gtc tcc cgt     144
Val Ile Pro Leu Ala Ser Ala Arg Leu Leu Ser Asp Lys Val Ser Arg
         35                  40                  45 gaa ctt tac ccg gtg gtg cat atc ggg gat gaa agc tgg cgc atg atg     192
Glu Leu Tyr Pro Val Val His Ile Gly Asp Glu Ser Trp Arg Met Met
     50                  55                  60 acc acc gat atg ggc agt gtg ccg gtc tcc gtt atc ggg gaa gaa gtg     240
Thr Thr Asp Met Gly Ser Val Pro Val Ser Val Ile Gly Glu Glu Val
 65                  70                  75                  80 gct gat ctc agc cac cgc gaa aat gac atc aaa aac gcc att aac ctg     288
Ala Asp Leu Ser His Arg Glu Asn Asp Ile Lys Asn Ala Ile Asn Leu
                 85                  90                  95 atg ttc tgg gga ata taa                                             306
Met Phe Trp Gly Ile
            100
```

<210> SEQ ID NO 2
<211> LENGTH: 420
<212> TYPE: DNA
<213> ORGANISM: Artificial Sequence
<220> FEATURE:
<221> NAME/KEY: CDS
<222> LOCATION: (1)...(378)
<223> OTHER INFORMATION: ccdB gene of pKIL 18.

<400> SEQUENCE: 2

```
atg acc atg att acg aat tcg agc tcg gta ccc ggg gat cct cta gag      48
Met Thr Met Ile Thr Asn Ser Ser Ser Val Pro Gly Asp Pro Leu Glu
 1               5                  10                  15 tcg acc tgc agg cat gca agc ttg tct ttg cag ttt aag gtt tac acc      96
Ser Thr Cys Arg His Ala Ser Leu Ser Leu Gln Phe Lys Val Tyr Thr
             20                  25                  30 tat aaa aga gag agc cgt tat cgt ctg ttt gtg gat gta cag agt gat     144
Tyr Lys Arg Glu Ser Arg Tyr Arg Leu Phe Val Asp Val Gln Ser Asp
         35                  40                  45 att att gac acg ccc ggg cga cgg atg gtg atc ccc ctg gcc agt gca     192
Ile Ile Asp Thr Pro Gly Arg Arg Met Val Ile Pro Leu Ala Ser Ala
     50                  55                  60 cgt ctg ctg tca gat aaa gtc tcc cgt gaa ctt tac ccg gtg gtg cat     240
Arg Leu Leu Ser Asp Lys Val Ser Arg Glu Leu Tyr Pro Val Val His
```

```
                65                  70                  75                  80
atc ggg gat gaa agc tgg cgc atg atg acc acc gat atg gcc agt gtg        288
Ile Gly Asp Glu Ser Trp Arg Met Met Thr Thr Asp Met Ala Ser Val
                    85                  90                  95 ccg gtc tcc gtt atc ggg gaa gaa gtg gct gat ctc agc cac cgc gaa        336
Pro Val Ser Val Ile Gly Glu Glu Val Ala Asp Leu Ser His Arg Glu
                100                 105                 110 aat gac atc aaa aac gcc att aac ctg atg ttc tgg gga ata                378
Asn Asp Ile Lys Asn Ala Ile Asn Leu Met Phe Trp Gly Ile
        115                 120                 125 taaatgtcag gctccgttat acacaagcta gcttggcact gg                         420

<210> SEQ ID NO 3
<211> LENGTH: 416
<212> TYPE: DNA
<213> ORGANISM: Artificial Sequence
<220> FEATURE:
<221> NAME/KEY: CDS
<222> LOCATION: (1)...(378)
<223> OTHER INFORMATION: ccdB gene of plasmid pKIL 19.

<400> SEQUENCE: 3 atg acc atg att acg cca agc ttg cat gcc tgc agg tcg act cta gag         48
Met Thr Met Ile Thr Pro Ser Leu His Ala Cys Arg Ser Thr Leu Glu
1               5                   10                  15 gat ccc cgg gta ccg agc tcg aat tca ttg cag ttt aag gtt tac acc         96
Asp Pro Arg Val Pro Ser Ser Asn Ser Leu Gln Phe Lys Val Tyr Thr
                20                  25                  30 tat aaa aga gag agc cgt tat cgt ctg ttt gtg gat gta cag agt gat        144
Tyr Lys Arg Glu Ser Arg Tyr Arg Leu Phe Val Asp Val Gln Ser Asp
            35                  40                  45 att att gac acg ccg ggg cga cgg atg gtg atc ccc ctg gcc agt gca        192
Ile Ile Asp Thr Pro Gly Arg Arg Met Val Ile Pro Leu Ala Ser Ala
        50                  55                  60 cgt ctg ctg tca gat aaa gtc tcc cgt gaa ctt tac ccg gtg gtg cat        240
Arg Leu Leu Ser Asp Lys Val Ser Arg Glu Leu Tyr Pro Val Val His
65                  70                  75                  80 atc ggg gat gaa agc tgg cgc atg atg acc acc gat atg gcc agt gtg        288
Ile Gly Asp Glu Ser Trp Arg Met Met Thr Thr Asp Met Ala Ser Val
                    85                  90                  95 ccg gtc tcc gtt atc ggg gaa gaa gtg gct gat ctc agc cac cgc gaa        336
Pro Val Ser Val Ile Gly Glu Glu Val Ala Asp Leu Ser His Arg Glu
                100                 105                 110 aat gac atc aaa aac gcc att aac ctg atg ttc tgg gga ata                378
Asn Asp Ile Lys Asn Ala Ile Asn Leu Met Phe Trp Gly Ile
        115                 120                 125 taaatgtcag gctccgttat acacgaatta attcagtg                              416

<210> SEQ ID NO 4
<211> LENGTH: 101
<212> TYPE: PRT
<213> ORGANISM: Artificial Sequence
<220> FEATURE:
<223> OTHER INFORMATION: ccdB protein of plasmid F

<400> SEQUENCE: 4

Met Gln Phe Lys Val Tyr Thr Tyr Lys Arg Glu Ser Arg Tyr Arg Leu
1               5                   10                  15

Phe Val Asp Val Gln Ser Asp Ile Ile Asp Thr Pro Gly Arg Arg Met
                20                  25                  30

Val Ile Pro Leu Ala Ser Ala Arg Leu Leu Ser Asp Lys Val Ser Arg
```

```
                35                    40                    45
Glu Leu Tyr Pro Val Val His Ile Gly Asp Glu Ser Trp Arg Met Met
         50                    55                    60
Thr Thr Asp Met Gly Ser Val Pro Val Ser Val Ile Gly Glu Glu Val
 65                    70                    75                    80
Ala Asp Leu Ser His Arg Glu Asn Asp Ile Lys Asn Ala Ile Asn Leu
                 85                    90                    95
Met Phe Trp Gly Ile
                100

<210> SEQ ID NO 5
<211> LENGTH: 126
<212> TYPE: PRT
<213> ORGANISM: Artificial Sequence
<220> FEATURE:
<223> OTHER INFORMATION: ccdB protein from plasmid pKIL 18.

<400> SEQUENCE: 5

Met Thr Met Ile Thr Asn Ser Ser Val Pro Gly Asp Pro Leu Glu
 1               5                   10                  15
Ser Thr Cys Arg His Ala Ser Leu Ser Leu Gln Phe Lys Val Tyr Thr
                 20                    25                    30
Tyr Lys Arg Glu Ser Arg Tyr Arg Leu Phe Val Asp Val Gln Ser Asp
                 35                    40                    45
Ile Ile Asp Thr Pro Gly Arg Arg Met Val Ile Pro Leu Ala Ser Ala
                 50                    55                    60
Arg Leu Leu Ser Asp Lys Val Ser Arg Glu Leu Tyr Pro Val Val His
 65                    70                    75                    80
Ile Gly Asp Glu Ser Trp Arg Met Met Thr Thr Asp Met Ala Ser Val
                 85                    90                    95
Pro Val Ser Val Ile Gly Glu Val Ala Asp Leu Ser His Arg Glu
                100                   105                   110
Asn Asp Ile Lys Asn Ala Ile Asn Leu Met Phe Trp Gly Ile
                115                   120                   125

<210> SEQ ID NO 6
<211> LENGTH: 126
<212> TYPE: PRT
<213> ORGANISM: Artificial Sequence
<220> FEATURE:
<223> OTHER INFORMATION: ccdB protein from pKIL 19.

<400> SEQUENCE: 6

Met Thr Met Ile Thr Pro Ser Leu His Ala Cys Arg Ser Thr Leu Glu
 1               5                   10                  15
Asp Pro Arg Val Pro Ser Ser Asn Ser Leu Gln Phe Lys Val Tyr Thr
                 20                    25                    30
Tyr Lys Arg Glu Ser Arg Tyr Arg Leu Phe Val Asp Val Gln Ser Asp
                 35                    40                    45
Ile Ile Asp Thr Pro Gly Arg Arg Met Val Ile Pro Leu Ala Ser Ala
                 50                    55                    60
Arg Leu Leu Ser Asp Lys Val Ser Arg Glu Leu Tyr Pro Val Val His
 65                    70                    75                    80
Ile Gly Asp Glu Ser Trp Arg Met Met Thr Thr Asp Met Ala Ser Val
                 85                    90                    95
Pro Val Ser Val Ile Gly Glu Val Ala Asp Leu Ser His Arg Glu
                100                   105                   110
```

-continued

```
Asn Asp Ile Lys Asn Ala Ile Asn Leu Met Phe Trp Gly Ile
        115                 120                 125

<210> SEQ ID NO 7
<211> LENGTH: 31
<212> TYPE: DNA
<213> ORGANISM: Artificial Sequence
<220> FEATURE:
<223> OTHER INFORMATION: kid1 primer.

<400> SEQUENCE: 7
gaggaattca ttgggaaaga ggggaaatct g                           31

<210> SEQ ID NO 8
<211> LENGTH: 29
<212> TYPE: DNA
<213> ORGANISM: Artificial Sequence
<220> FEATURE:
<223> OTHER INFORMATION: kid2 primer.

<400> SEQUENCE: 8
gaggaattct caagtcagaa tagtggaca                              29

<210> SEQ ID NO 9
<211> LENGTH: 30
<212> TYPE: DNA
<213> ORGANISM: Artificial Sequence
<220> FEATURE:
<223> OTHER INFORMATION: kid3 primer.

<400> SEQUENCE: 9
gagaagctta ttggaaagag gggaaatctg                             30

<210> SEQ ID NO 10
<211> LENGTH: 29
<212> TYPE: DNA
<213> ORGANISM: Artificial Sequence
<220> FEATURE:
<223> OTHER INFORMATION: kid4 primer.

<400> SEQUENCE: 10
gagaagcttt caagtcagaa tagtggaca                              29
```

CLONING AND/OR SEQUENCING VECTOR

RELATED APPLICATIONS

This application is a continuation-in-part of Application Ser. No. 08/379,614 filed Jul. 20, 1995, now U.S. Pat. No. 5,910,438, which is the U.S. National Phase under 35 U.S.C. Section 371 of International Application PCT/BE93/00051, filed Aug. 2, 1993 which claims priority of Application BE 09200696, filed Jul. 31, 1992.

SUBJECT-MATTER OF THE INVENTION

The invention relates to a cloning and/or sequencing vector which enables recombinant clones to be selected directly.

The invention also relates to the procaryote cell which is transformed by this vector and to the procaryote host cell for this vector, as well as to the use of this cloning and sequencing vector for selecting and sequencing recombinant clones.

STATE OF THE ART AND TECHNOLOGICAL BACKGROUND UNDERLYING THE INVENTION

Phage (the M13 series) and plasmid (the pUC series) cloning vectors, containing numerous unique cloning sites, were constructed by Messing et al (P.N.A.S. USA, 79, pp. 3642–3646 (1977), by Norrander et al (Gene, 26, pp. 101–106 (1983) and Yanisch-Perron et al (Gene, 33 pp. 103 to 119) (1985))

The multiple cloning sites (MCS—multiple cloning sites) of these vectors are located in the coding sequence of the LacZ gene.

Discrimination between the transformed cells which harbour a recombinant vector and the cells which harbour a non-recombinant vector is achieved using the "blue screen" technique described by Gronenborn and Messing (Methylation of single-stranded DNA in vitro introduces new restriction endonuclease cleavage sites, Nature, 272, pp. 375–377 (1978)).

However, this "blue screen" technique suffers from the disadvantage of using a screening procedure (discrimination) rather than a procedure for selecting the clones.

Discrimination by screening is based on identifying a clone within a population of clones on the basis of a characteristic (color) which differentiates it. Selection has no need of this characteristic, since it is only recombinant clones which are isolated by this method.

The screening procedure is based on the color of the recombinant clones (white color) and of the non-recombinant clones (blue color). This color is based on inactivation of the marker beta-galactosidase, preventing cleavage of X-gal (5-bromo-4-chloro-3-indolyl β-galactoside). The cell colonies harbouring a non-recombinant vector produce a functional beta-galactosidase and, by hydrolysing the X-gal substrate, produce a blue coloration. In general, the insertion of a DNA fragment into the β-galactosidase gene prevents cleavage of the X-gal. For this reason, the cells harbouring a recombinant vector have a white color.

Moreover, this complex procedure requires the use of the substrate X-gal which is a product which is very expensive, unstable and awkward to use.

On the other hand, various cloning vectors permitting direct selection (positive selection) of recombinant strains have been described in the scientific literature.

Pierce et al (Proc. Natl. Acad. Sci., vol 89. No. 6, 1992, pp. 2056–2060) describe a vector which comprises the lethal gene sacB from Bacillus amylolique-faciens, integrated into a plasmid derived from the bacteriophage P1 and under the control of a specific *E. coli* promoter.

The promoter of this vector includes a region having several specific cloning sites (cleavage site for a restriction enzyme).

Since the gene sacB encodes levan sucrase, which catalyses the hydrolysis of sucrose into products which are toxic for *E. coli*, direct selection of the mutants which incorporate a recombinant plasmid is effected on a culture medium containing sucrose. Since the levan sucrase is toxic, even in the absence of sucrose, it is essential, consequently, to repress its synthesis if one wishes to obtain a large number of plasmid copies in the bacterial cytoplasm.

However, it is difficult, if not impossible, to repress the cytotoxic gene completely, particularly if a large number of copies of the vector are required.

Therefore, the impossibility of repressing the cytotoxic gene leads, in phases of producing the plasmid, to the death of the cell and, as a consequence, to selective pressure towards mutated strains (characterised by an inactive lethal gene).

In this case, in order to ensure that the enzyme encoded by the sacB gene does not kill the host cell, it is necessary to incorporate a CI repressor, which regulates the expression of this gene, into the cloning vector.

Furthermore, since sucrose is often incorporated into bacterial culture media, it will be essential to prepare media which are totally free of sucrose in order to carry out these manipulations.

Henrich et al (Gene, vol 42, No. 3, 1986, pp. 345–349) describe a vector which includes the E gene from the bacteriophage ΦX174, the said E gene being incorporated into the plasmid pUH84 under the control of the Lac promoter.

In this case, the E gene includes six unique restriction sites (located over the whole of the E gene sequence) and encodes gpE, which causes lysis of the *E.coli* cell. In this case, positive selection is effected when a foreign recombinant gene has been inserted into one of the restriction sites.

However, this insertion of a foreign gene into a restriction site located in the sequence of the E gene, encoding gpE, makes it more difficult to sequence the foreign gene and/or amplify it by PCR since, in this case, portions of useless sequences belonging to the E gene encoding gpE are also sequenced, amplified and characterised.

Kuhn et al (Gene, vol 42, No. 3, 1986, pp. 253–263) describe a vector which includes a large gene encoding a restriction enzyme which kills by cleaving the genome of the bacterium, the said gene being incorporated into the plasmid pKG2 under the control of the LacUV5 promoter.

The cloning vectors of the state of the art suffer from the disadvantage of having to be maintained in a host strain which includes the LacI$^q$ repressor in episomal form, or the CI repressor, in order to inactivate the promoter and prevent expression of the killer gene, leading to the death of the host strain.

In addition, if it is desired to use this strain to produce a large number of copies of the cloning vectors, the repressor will not be adequate for preventing either a selective pressure which modifies the cytotoxic activity of the vector or a "genetic leakage", that is to say expression of certain copies of the vector and death of the host strain.

Consequently, none of the documents of the state of the art describes a cloning vector which can incorporate large nucleotide fragments, which is easy to manipulate and which can be produced by a micro-organism on an industrial scale; that is to say, which can be produced in a large number of copies by a micro-organism without bringing about the death of the latter.

OBJECTS OF THE INVENTION

The present invention aims to supply a novel cloning and/or sequencing vector, and also its host strain, which are simple and relatively inexpensive to construct and produce, and which enable recombinant clones to be selected directly, without suffering from the disadvantages of the above-mentioned state of the art.

A particular object of the present invention is to obtain a vector which permits specific and certain selection of the recombinant clones.

Another object of the present invention is directed towards obtaining a vector which permits the sequencing, amplification and/or characterisation, using the same primer, of any foreign DNA fragment (whatever its size) in the recombinant clones.

An additional object of the present invention is directed towards obtaining a vector which also permits simple extraction of this foreign DNA fragment from the recombinant clone.

A final object of the present invention is directed towards obtaining a host strain for the said vector which allows a large number of copies of the said vector to be produced without bringing about selective pressure which modifies the cytotoxic activity of the said vector or causing the death of the host strain.

CHARACTERISTIC ELEMENTS OF THE INVENTION

The invention relates to a novel cloning and/or sequencing vector which includes, incorporated into an autonomously replicating vector, at least one promoter nucleotide sequence and at least one nucleotide sequence encoding a fusion protein which is active as a poison, the said nucleotide sequence being obtained by fusing a coding nucleotide sequence which includes several unique cloning sites and a nucleotide sequence which encodes a protein poison.

Preferably, the autonomously replicating vector is a recombinant virus or a recombinant plasmid such as a pUC plasmid.

The promoter nucleotide sequence can comprise any promoter, which permits expression of the nucleotide sequence encoding a fusion protein which is active as a poison.

Preferably, this promoter nucleotide sequence consists of the Lac operon promoter.

According to one preferred embodiment of the invention, the unique cloning sites (MCS) of the nucleotide sequence which is fused to the nucleotide sequence which encodes the protein poison are absent from the remainder of the nucleotide sequence of the vector according to the invention.

Advantageously, the nucleotide sequence of the gene which encodes the protein poison comprises all or part of the nucleotide sequence of the wild-type gene which encodes the protein CcdB or the protein Kid.

Preferably, the nucleotide sequence of the gene which encodes the protein poison lacks the cleavage site for the restriction enzyme SmaI.

Another aspect of the invention relates to a procaryote cell which is transformed with the cloning vector according to the invention.

The invention also relates to a procaryote host cell for the vector according to the invention which possesses a chromosomal $I^q$ and an elevated transformation efficiency, and which possesses a mutation conferring resistance to the poison activity of the fusion protein, and/or which possesses a gene encoding a protein which is an antipoison to the fusion protein.

Preferably, the procaryote host cell for the vector according to the invention possesses a mutation in the gene encoding subunit A, or in the gene encoding subunit B, of the gyrase, and conferring resistance to the fusion protein, and/or a gene which encodes the protein CcdA which is an antipoison to the fusion protein comprising CcdB and/or encodes the protein Kis which is an antipoison of the fusion protein comprising Kid.

Preferentially, the procaryote cell is an *Escherichia coli* cell which possesses a mutation which is responsible for replacing arginine 462 with a cysteine in the amino acid sequence of the GyrA polypeptide of the gyrase, thereby conferring resistance to the fusion protein.

Preferably, this procaryote host cell also possesses the $LacI^q$ mutation.

The present invention also relates to fragments of the vector according to the invention, in particular primers for sequencing and/or amplifying (for example by PCR) the foreign nucleotide fragments inserted into the vector according to the invention.

Preferably, these primers consist of sequences of from 10 to 30 nucleotides which hybridise to nucleotide sequences which are situated on either side of the nucleotide sequence of the vector according to the invention which contains several unique cloning sites.

A final aspect of the invention relates to the use of the vector according to the invention for selecting and sequencing recombinant clones.

DESCRIPTION OF A PREFERRED EMBODIMENT OF THE INVENTION

Figure 1:
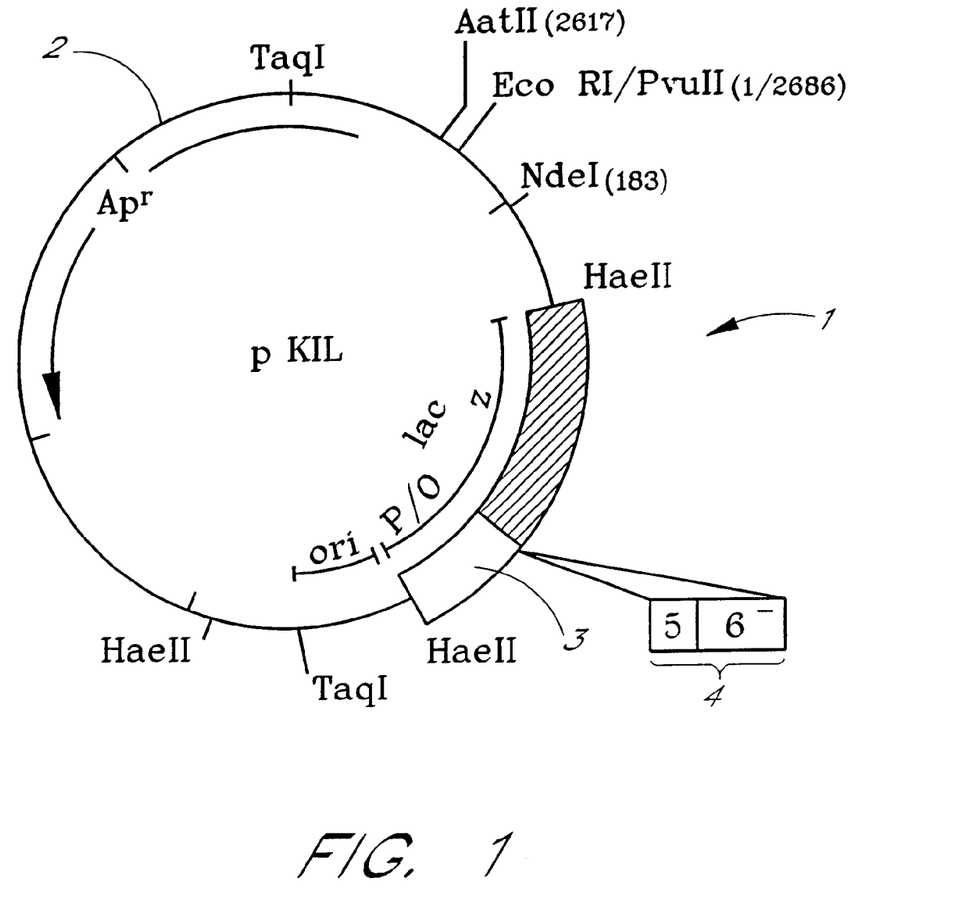
FIG. 1 is a diagrammatic representation of a cloning vector according to the Present invention.

According to the invention, the cloning and/or sequencing vector 1 includes, incorporated into an autonomously replicating vector 2, at least one promoter nucleotide sequence 3 and at least one nucleotide sequence 4 which encodes a fusion protein which is active as a poison, the said nucleotide sequence 4 being obtained by fusing a coding nucleotide sequence 5 (or polylinker) which encompasses several (multiple) unique cloning sites (MCS), and a nucleotide sequence (6) which encodes a protein poison.

An autonomously replicating vector 2 is understood to mean any nucleotide construct, such as a virus or a plasmid (preferably a recombinant plasmid of the PUC series), which is capable of being introduced into a micro-organism, of recombining therein and/or of replicating therein.

FIG. 1 shows a diagrammatic representation of a cloning vector according to the present invention, which vector is constructed from a plasmid of the pUC series (pUC18 and pUC19), which is described by Norrander et al (Construction of improved M13 vectors using oligo-deoxinucleotide-directed mutagenesis, Gene, 26, pp.

101–106 (1983)) and by Yanisch-Perron et al (Improved M13 phage cloning vectors and host strains-. nucleotide sequences of the M13mp18 and pUC19 vectors, Gene, 33, pp. 103–119 (1985)).

A coding nucleotide sequence 5 encompassing several (multiple) unique cloning sites (MCS) is understood to mean a short coding sequence (or polylinker) which comprises several cleavage sites for restriction enzymes.

The advantage of having a polylinker in the vector according to the invention is that different cloning sites are located on a single short sequence, thereby permitting:
rapid sequencing and amplification, using the same primers, of any DNA fragment which is inserted into this vector, rapid extraction of the cloned fragment, facilitated by the proximity of the restriction sites. Thus, in contrast to the state of the art, this proximity avoids sequencing, amplifying and characterising useless fragments from other sequences of the vector according to the invention.

Nucleotide sequence 6 encoding a protein poison is understood to mean any (wild-type) nucleotide structure encoding a protein which displays an activity which is naturally poisonous and specific for one or more vital functions of a host cell.

A protein poison is also characterised by the existence of an antidote or antipoison, such as the proteins CcdB and CcdA, the protein Kid and its antagonist Kis, the protein PemK and its antagonist PemI, the protein Doc and its antagonist Phd, the protein HoK and its antagonist Sok, and other poison molecules which are, or are not, of plasmid origin.

In this case, the nucleotide sequence 6 encoding a protein poison consists of the wild-type gene CcdB, which encodes the protein CcdB (control of cell death), obtained from the ccd locus of the F plasmid (SEQ ID NO:1 and SEQ ID NO:4).

The ccd locus of the F plasmid comprises the two wild-type genes ccdA and ccdB, also termed H and G, or letA and letD, which respectively encode proteins of 72 and 101 amino acids (Bex et al, Mini-F encoded proteins; identification of a new 10.5 kilodalton species. EMBO J.2, 1853–1861 (1983); Miki et al, Control of cell division by sex factor F in *Escherichia coli*. I. The 42.84–43.6 F segment couples cell division of the host bacteria with replication of plasmid DNA, J. Mol. Bio., 174, 605–625, (1984)).

In *Escherichia coli*, the CcdB protein of the F plasmid is a cytotoxin whose lethal activity is counteracted by the protein CcdA (Karoui et al, Ham22, a mini-F mutation which is lethal to host cell and promotes recA- dependent induction of lambdoid prophage. EMBO J.2, 1863–1868 (1983); Ogura and Hiraga Mini-F plasmid gene that couple host cell division to plasmid proliferation, Proc. Natl. Acad. Sci. USA, 80, 4784–4788 (1983); Miki et al, Control of cell division by sex factor F in *Escherichia coli*. Identification of genes for inhibitor protein and trigger protein on the 42.84–43.6F segment, J. Mol. Biol. 174, 627–646 (1984b)).

The molecular mechanism by which protein CcdB exerts its lethal activity has been elucidated; protein CcdB is poisonous to DNA topoisomerase II.

The type II DNA topoisomerases are essential and ubiquitous enzymes which alter the topology of the DNA by transiently introducing a double-stranded break into the DNA. During the stage of break-religation, topoisomerase II forms an intermediate complex with its DNA substrate in which the enzyme is attached covalently to the 5' end of the cleaved DNA, This transitory intermediate, in which topoisomerase II is linked covalently to the DNA, has been termed the "cleavable complex" (Wang, DNA topoisomerases. Annu. Rev. Biochem. 54, 665–97, 1985; Maxwell & Gellert, Mechanistic aspects of DNA topoisomerases. Advan. Protein Chem. 38, 69–107, 1986; Liu, DNA topoisomerase poisons as antitumor drugs, Annu. Rev. Biochem. 58. 351–375, 1989).

Both in eucaryotes and in procaryotes, the cleavable topoisomerase II-DNA complex is the target of powerful therapeutic agents, including the antibiotics of the "quinolone" family, which act on the gyrase (bacterial topoisomerase II), and anticancer agents (acridines and epipodophyllotoxins), which act on the mammalian topoisomerase II. The therapeutic efficacy of the topoisomerase poisons is correlated with their ability to stabilise the cleavable complex.

DNA topoisomerase IT is an essential enzyme in all living entities and is very conserved in the evolution of the species. The CcdB protein thus displays an activity which is potentially cytotoxic for a wide variety of procaryote species.

The small size of the wild-type ccdB gene allows it to be inserted into plasmids without increasing their size excessively and consequently allows large fragments of foreign DNA to be included therein, Furthermore, given its small size, the wild-type ccdB gene of the F plasmid contains very few restriction sites; it is, therefore, simpler to preserve the uniqueness of the multiple cloning sites (MCS) which are added to it.

Unexpectedly, the inventors observed that the in-phase fusion of the nucleotide sequence 6, encoding protein CcdB, with the coding nucleotide sequence (polylinker 5), comprising several (multiple) unique cloning sites (MCS) gave a nucleotide sequence 4 which encodes a fusion protein which is active as a poison and which makes it possible, as a consequence, to produce vectors for the direct selection of recombinant plasmids (killer selection).

The plasmids which have been obtained allow doubly digested restriction fragments to be cloned in both orientations with respect to the lac promoter. Insertion of a restriction fragment into one of the unique cloning sites interrupts the genetic information of the gene fusion, leading to the synthesis of a gene fusion product which is not functional. Insertional inactivation of the gene fusion ought always to take place when a termination codon is introduced or when a change is made in the reading frame.

The cells which harbour an intact cloning vector of this nature produce a poisonous fusion protein which is functional, and die.

Insertion of a foreign DNA fragment into one of the unique cloning sites of the gene fusion interferes with production of the poison.

The cells which harbour a recombinant vector will be viable while cells which harbour an intact vector will not be viable. This killer selection, by simple culture on a solid medium, makes it possible to eliminate cells which harbour a non-recombinant vector (non-viable clones) and to select recombinant clones (viable clones).

EXAMPLE I

Construction of the plasmid pKIL19

The ccdB gene was amplified by PCR using, as DNA template, the plasmid pULB2208 (Bernard and Couturier, The 41 carboxy-terminal residues of the miniF plasmid CcdA protein are sufficient to antagonise the killer activity of the CcdB protein, Mol. Gen. Genet. 226, 297–304 (1991) as well as synthetic oligonucleotides.

The synthetic oligonucleotide sequences were selected in such a way as to create an EcoRI restriction site on either side of the wild-type ccdB gene in order to be able to reclone this gene in frame with the codons of the MCS19 multiple cloning site and to eliminate the initiation codon of the native ccdB gene. The DNA resulting from the PCR reaction was digested with the enzyme EcoRI and cloned into the EcoRI site of the plasmid pUC19. The resulting plasmid, in which the EcoRI fragment was integrated in the orientation which permitted the ccdB gene, provided with the additional codons corresponding to the MCS19 multiple cloning sites, to be read from the Lac promoter, was termed pKIL2. Plasmid pKIL2 is lethal for a wild-type bacterium (Ccdb$^S$ sensitive). pKIL2 also possesses two SmaI sites, one in the multiple cloning sites and the other in the central region of the ccdB gene. The latter was eliminated by site-directed mutagenesis. The resulting plasmid pKIL3, having a unique SmaI site, still has two EcoRI sites. The EcoRI site downstream of the ccdB gene was eliminated by filling in its cohesive ends.

The resulting plasmid, pKIL19 (SEQ ID NO:2 and SEQ ID NO:5), thus possesses a unique EcoRI restriction site within seqnnce 5, which encompasses the multiple cloning site.

EXAMPLE II
Construction of the plasmid pKIL18

The ccdB gene was amplified by PCR using, as DNA template, plasmid pKIL19 as well as synthetic oligonucleotides. The sequences of the synthetic oligonucleotides were selected in such a way as to create a HindIII site on either side of the ccdB gene in order to be able to reclone this gene in frame with the codons of the MCS18 multiple cloning sites. The DNA resulting from the PCR reaction was digested by the enzyme HindIII and cloned into the HindIII site of the plasmid pUC18. The resulting plasmid, in which the HindIII fragment was integrated in the orientation which permitted the ccdB gene, provided with the additional codons corresponding to the MCS18 multiple cloning sites, to be read from the Lac promoter, was termed pKIL4. Plasmid pKIL4 is lethal for a Ccdb$^S$-sensitive bacterium.

The HindIII site downstream of the ccdB gene was eliminated by filling in its cohesive ends. The resultant plasmid, pKIL18 ((SEQ ID NO;4 and SEQ ID NO:6), possesses a unique HindIII restriction site as well as a unique SmaI site (since constructed from pKIL19).

EXAMPLE III
Construction of the plasmid pKID18

ParD is a killer stability system of R1 plasmid located in the proximity of the basic replicon. It is a small operon containing two genes, Kid and Kis, coding for a killer component and its antagonist respectively (Bravo et al., Mol. Gen. Genet., Vol. 215, pp. 146–151 (1988)). This system is perfectly conserved and functional in another incFII plasmid, R100 (pem system: Tsuchimoto et al., J. of Bacteriol., Vol. 170, pp. 1461–1466 (1988)), PemA (identical to Kis) and PemB (identical to Kid).

The vectors pKID18 and pKID19 contain the Kid gene fused to different polylinkers (MCS18 and MSC19 for pKID18 and pKID19 respectively). The Kid sequence was amplified by PCR from the plasmid R1 drd19 using the primers kid1-gaggaattcattgggaaagagggaaatctg-(SEQ ID NO:7) and kid2 -gaggaattctcaagtcagaatagtggaca-(SEQ ID NO: 8). The generated insert was cloned into the EcoRI site of pUC19 (Yanish-Perron et al. (1985)). This insertion generates a fusion gene between the MCS19 and Kid. The vector pKID18 was obtained as follows: the Kid sequence was amplified by PCR from the plasmid R1 drd19 using the primers kid3-gagaagcttattggaaagagggaaatctg-(SEQ ID NO:9) and kid4-gagaagctttcaagtcagaatagtggaca-(SEQ ID NO:10). The generated insert was cloned into the HindIII site of pUC18 (Yanish-Perron et al. (1985)). This insertion generates a fusion gene between the MCS18 and Kid.

In induce conditions (induction of the pLac) that control the fuse Kid transcription of this construct for the *E. coli* strain (Top-10 F Invitrogen), this vector which contains the Kid gene fused to different polylinkers has retained the poison activity of the original Kid protein.

The regulation and the expression of this vector in a specific cell which is not killed by the poison activity of the fusion protein can be obtained by a control of the promoter activity of said vector or can be obtained by the production of said vector in a cell expressing the Kis protein which is the antidote of the Kid protein.

EXAMPKLE IV
Construction of the strains Ccdb$^4$ and Ccdb$^S$

In order to be able to maintain plasmids pKIL18 and pKIL19 within a bacterium, the latter has to be resistant to the lethal effect of the fusion protein which is active as a poison, Unexpectedly, the chromosomal mutation gyrA462 confers on the strains total resistance to the poisonous effect of the fusion protein.

Moreover, since plasmids pKIL18 and pKIL19 derive directly from plasmids pUC18 and pUC19 and express the ccdB genes from the Lac promoter, it is preferable to maintain these plasmids in a LacI$^q$ strain. Thus, while, in our case, continuous overexpression of these genes does not exert a selection pressure in favour of certain mutations, the LacI$^q$ strain allows expression from the Lac promoter to be reduced and conserves the bacterial machinery, thereby guaranteeing a rapid generation time (increased production of the vector by the strain), The strain D1210 (Sadler et al Gene 8, pp. 279–300 (1980)), derived from the strain HB101 LacI$^q$, LacY$^+$ (Maniatis et al Molecular Cloning Laboratories Man. Cold Spring Harbour Laboratory N.Y.), and characterised by a chromosomal I$^q$ and increased transformation efficiency, was transformed with the plasmid pCOS2.1. This plasmid, which confers resistance to kanamycin, carries the recA gene from Erwinia chrysanthemi 3665 and allows recombination in *E, coli*. A lysate of P1 phage was prepared on a Ccdb$^R$ gyrA462, zei298::Tn10 strain and used to infect the strain D1210/pCOS2.1. The transductants which were resistant to tetracycline were selected and tested for their resistance or sensitivity to the CcdB protein. One of the Ccdb$^R$ transductants was then cured of plasmid pCOS2.1 and termed KIB22.

Strain KI322 constitutes an ideal host strain for plasmids pKIL18 and pKIL19 while strain D1210 constitutes the ideal host for selecting recombinant plasmids.

Thus, strain KIB22 advantageously possesses an elevated efficiency of DNA extraction (comparable to the yield of the pUC plasmids) and, unexpectedly, resistance to the fusion protein which is encoded by pKIL18 and pKIL19.

Consequently, it is possible to use this micro-organism to produce the cloning vector according to the invention on an industrial scale in numerous copies without causing the death of the said micro-organism.

The selection is carried out simply by spreading the bacteria on a medium containing IPTG (Isopropyl-Beta-D-thiogalactopyranoside) as well as ampicillin.

Strain KIB22 was deposited with the Laboratorium voor Microbiologie-Bacteriënverzameling (LMG) [Microbiological Laboratory—Bacterial Collection] of the Belgian Coordinated Collections of Microorganisms (BCCM) under No. LMG P-12601.

The cloning vector pKIL19 was deposited with the Laboratorium voor Moleculaire Biologie-Plasmiden Collectie (LMBP) [Molecular Biological Laboratory—Plasmid Collection] of the Belgian Coordinated Collections of Microorganisms (BCCM) under the No. LMBP 2781.

These depositions were made in accordance with the provisions of the Budapest Treaty regarding the International Recognition of the Deposition of Microorganisms.

What is claimed is:

1. An autonomously replicating cloning and/or sequencing vector adapted to transform a procaryotic cell, said vector comprising at least one promoter and at least one nucleotide sequence which encodes a fusion protein which is active as a poison to the procaryotic cell, said nucleotide sequence which encodes the fusion protein being obtained by fusing a coding nucleotide sequence which comprises several cloning sites, and a nucleotide sequence which encodes a protein poison.

2. The autonomously replicating cloning and/or sequencing vector of claim 1, wherein said vector is a recombinant virus.

3. The autonomously replicating cloning and/or sequencing vector of claim 1, wherein said vector is a recombinant plasmid.

4. The autonomously replicating cloning and/or sequencing vector of claim 1, wherein said promoter comprises the Lac operon promoter.

5. An autonomously replicating cloning and/or sequencing vector adapted to transform a procaryotic cell, according to claim 1, wherein at least one of said cloning sites is a unique cloning site which is absent on the remainder of the cloning vector.

6. An autonomously replicating cloning and/or sequencing vector according to claim 1, wherein the nucleotide sequence which encodes a protein poison encodes the protein poison Kid.

7. The vector according to claim 1, wherein the nucleotide sequence which encodes the protein poison lacks a cleavage site for the restriction enzyme SmaI.

8. A procaryotic cell which is transformed by a cloning vector according to claim 1.

9. A method for selecting recombinant clones, comprising the steps of:

inserting an oligodeoxynucleotide into the coding nucleotide sequence of the vector according to claim 1, transforming a procaryotic cell susceptible to the poison protein with the vector, and selecting recombinant clones which survive.

10. The autonomously replicating cloning and/or sequencing vector of claim 3, wherein said vector is a pUC plasmid.

11. A procaryotic host cell, comprising a cloning vector which encodes a fusion protein obtained by fusing a coding nucleotide sequence which comprises several cloning sites and a nucleotide sequence which encodes a protein poison, wherein the cell possesses a mutation which confers resistance to the poison activity of the fusion protein and/or possesses a gene which encodes a protein which is an antipoison to the fusion protein.

12. The cell according to claim 11, wherein the cell possesses a $LacI^q$ mutation.

13. A procaryotic host cell, according to claim 11, wherein the fusion protein encodes a poison to which the protein CcdA is an antipoison and wherein the cell possesses a gene which encodes the protein CcdA.

14. A procaryotic host cell, according to claim 11, wherein the fusion protein encodes a poison to which the protein Kis is an antipoison and wherein the cell possesses a gene which encodes the protein Kis.

* * * * *

UNITED STATES PATENT AND TRADEMARK OFFICE
CERTIFICATE OF CORRECTION

PATENT NO.   : 6,180,407 B1                                     Page 1 of 1
DATED        : January 30, 2001
INVENTOR(S)  : Philippe Bernard and Philippe Gabant It is certified that error appears in the above-identified patent and that said Letters Patent is hereby corrected as shown below:

<u>Title page,</u>
Item [22], please replace "Jan. 4, 1998" with -- Jan. 4, 1999 --.

Signed and Sealed this

Twenty-fifth Day of February, 2003

JAMES E. ROGAN
*Director of the United States Patent and Trademark Office*